United States Patent [19]

Root

[11] Patent Number: 4,832,814

[45] Date of Patent: May 23, 1989

[54] ELECTROFUSION CELL AND METHOD OF MAKING THE SAME

[75] Inventor: Richard T. Root, Elkton, Md.

[73] Assignee: E. I. Du Pont de Nemours and Company, Wilmington, Del.

[21] Appl. No.: 138,040

[22] Filed: Dec. 28, 1987

[51] Int. Cl.$^4$ .................... C12M 1/00; C12N 13/00; C12N 15/00

[52] U.S. Cl. ................ 204/299 R; 204/180.1; 435/287; 435/173; 435/172.2; 935/89; 935/93

[58] Field of Search ............... 435/173, 172.2, 172.1, 435/287, 289; 935/89, 91, 93, 94; 204/299 R, 180.1; 156/634, 645, 652, 656, 659.1; 430/320, 312, 313, 318, 325, 394

[56] References Cited

PUBLICATIONS

Masuda et al, Novel Methods of Cell Fusion and Handling Using Fluid Integrated Circuit—Electrostatics '87 (Proc. Int. Conf. on Electrostatics, Apr. 1987 in Oxford), Inst. Physics, London.

Masuda et al., Novel Methods of Cell Fusion in Field Construction Area in Fluid Integrated Circuit—to be Presented at IEEE/IAS 1987 Annual Conference, (Oct. 1987 in Atlanta, USA).

Masuda, S. "Novel Method of Cell Fusion in Field Constriction Area in Fluid Integrated Circuits" Conference Record of the 1987 IEEE Industry Applications Soceity Annual Meeting, Atlanta, Ga. 18–23 Oct. 1987 (abstracts only).

Primary Examiner—John F. Niebling
Assistant Examiner—John S. Starsiak, Jr.

[57] ABSTRACT

An apparatus and method of use is provided for the fusion of different cell types into hybrid cells through the use of electrofusion. The apparatus consists of thin-film electrodes etched onto an optically clear lower plate, a channel defined at its boundaries by a photocopolymer material laminated between the lower plate and an upper optically clear top plate providing closure of the channel as well as entry for the cells through the use of integral Luer ports. The apparatus may be produced, with minor adjustment, by using phototools.

16 Claims, 2 Drawing Sheets

ELECTROFUSION CELL AND METHOD OF MAKING THE SAME

BACKGROUND OF THE INVENTION

Within the past 5-6 years there has developed a great financial impetus for the high efficiency fusion of eucaryotic cells. This involves a technology that directly affects the production of monoclonal antibodies for clinical analyses, as well as for therapeutic and research uses. Production of hybrid plants and yeasts is another biotechnological area that is dependent on fusion of cells. The central aim in fusion hybridization is to create a hybrid of at least two different parental cell types which carries the desired genetic and phenotypic traits of the parents. An example would be the fusion of a lymphocyte capable of producing an antibody desired for a clinical immunoassay, with a myeloma cell capable of being grown in tissue culture.

At the present time the major methods of carrying out fusions of cells are through the use (1) of polyethylene glycol shock, (2) pH shock, or (3) electrically induced manipulations of the cell and cellular membranes (electrofusion). All of these methods require the use of a selective medium, through which use only hybrids expressing the appropriate genetic information from both parents are capable of growing. The first two methods involve the preparation of reagents which affect the integrity of the plasma membranes, and which may contain unknown toxic substances, thereby adversely affecting cell viability. These methods also depend on cells being brought into intimate proximity to each other via centrifugation into a dense pellet. Thus, although these are rather simple techniques, there is little control over the precise conditions employed and relatively high cell numbers are normally required, typically $1 \times 10^7$ cells or more. Nevertheless, both polyethylene glycol and pH shock are widely used today.

The third method, electrofusion, actually involves two phenomena of electrical effects on cells. The first is dielectrophoresis, a method of spatially manipulating of cells via the use of anisotropic radio frequency fields. This phenomenon has been excellently described by H. A. Pohl in the monograph *"Dielectrophoresis"*, Cambridge Monographs and Physics, 1978, Cambridge University Press, and is exploited to induce intimate inter-cell membrane contact via the formation of linear chains of cells usually referred to as pearl chains. The average number of cells comprising the chains may be controlled by adjusting the ratio of cells per milliliter to total available conductor length. Other pertinent variables are the frequency, intensity, and degree of anisotropy of the applied electric field. Once cell-cell contact is induced, fusion is brought about by the momentary interruption of the radio frequency field and the application of a high voltage direct current pulse. This pulse causes the reversible dielectric breakdown of the membranes only in the area of cell-cell contact. Upon cessation of the pulse the separate membranes recombine into a single one, causing the contents of the different cells to combine.

Integration of the separate genomes occurs during subsequent cell divisions, the result being a hybrid cell. The number of separate cells which fuse into one is termed the degree of karyogamy. The viability of the resulting hybrid decreases as the degree of karyogamy increases due to a process known as premature chromosomal condensation. Several references for this phenomenon are "*Mammalian Cell Fusion: Induction of Premature Chromosome Condensation in Interphase Nuclei*", by R. T. Johnson and P. N. Rao, Nature 226 (1970), pp. 717-722, and *Cellular Phase of Chromosome Pulverization Induced by Sendai Virus*, by H. Kato and A. A. Sandberg, J. Nat. 'l Cancer Inst. 41 (1968), pp. 1125-1131. It is therefore important to control the average length of the cell chains brought about by dielectrophoresis. The technique of electrofusion requires the use of various electronic equipment for producing the electric fields as well as a suitable chamber to contain the cells at optimal density and allow for exposure to the field. A review of this and other techniques is found in *Electric Field-Mediated Fusion and Related Electrical Phenomena*, by U. Zimmermann, Biochimica et Biophysica Acta, 694 (1982), pp. 227-277.

The presently available chambers fall into one of two categories. The first are simple glass or plastic microscope slides to which two parallel wires are cemented. This type is employed in determining the approximate optimal fields to cause dielectrophoretic alignment and fusion via simple observation. These cannot easily be kept sterile, which is a requirement if the hybrids are to be cultured. The second type is designed for the containment and fusion of large numbers of cells, usually greater than $1 \times 10^6$. These chambers are based upon several electrode types, with wires or flat plates typically being used. Typical of these prior chambers are those described in U.S. Pat. Nos. 4,516,961 and 4,578,167. Major disadvantages of these chambers are their inabilities to adjust the total length of effective electrode for different numbers of cell, for observation via microscopy and the inability to readily accommodate different volumes.

These disadvantages severely limit the utilization of this technique with pre-selected cell populations in which low numbers of cells are to be electrofused. For example, the selection of lymphoctye cells to obtain only those cells capable of producing an antibody to specific antigen with a specific binding constant can result in the collection of only 1 out of every $10^5$ to $10^6$ cells. Therefore, only 100 to 1000 cells could be collected from $1 \times 10^8$ original lymphocyte cells. If this number of cells were to be placed in a fusion chamber consisting of 322 cm of effective electrode length, the distribution resulting would insure that little or no cell-cell contact could be obtained by dielectrophoresis, and hence little or no hybrids would result. In fact, for 1000 cells, a chamber with less than 0.5 cm would be required.

It is necessary to provide an improved chamber design applicable to any number of cells which may be obtained by the various pre-selection techniques. It is furthermore desired that fusion may be affected in a batch in flow-through mode.

SUMMARY OF THE INVENTION

Many of the disadvantages of prior electrofusion chambers are overcome by the apparatus of this invention which is easily constructed. Such an apparatus for fusing cells comprises: a laminate formed by a first planar number, a grid of opposed electrodes coated on the first member, a second planar member, and a photopolymer, that is resistant to water, having a high dielectric, sandwiched between the first and second members, the photopolymer and members defining a cavity encompassing at least a portion of the opposed electrodes, means for applying electrical signals to the electrodes, and means in the second member defining a pair of ports for admitting and retrieving liquids and cells to and from the chamber.

In a preferred embodiment, the photopolymer is sheetlike and has a thickness in range of 0.01 to 0.02 cm thus defining a chamber of suitable height and yet can maintain even relatively low numbers of cells in proximity to the chamber electrodes for electrofusion. The apparatus provides for a wide range of total exposed electrode length and volumes for the maintenance of optimal density of cells per unit of conductor through a wide range of total cell numbers. The design does not limit the use of electrical, magnetic or ultrasonic methods to cause cell alignment prior to fusion, whether by a high voltage D.C. pulse or other techniques such as a laser beam. The apparatus can also be used to accommodate selection of cells through dielectrophoresis or lysis in high voltage electrical fields. The apparatus provides for the direct observation of the cells before, during, and after fusion, in a manner consistent with the maintenance of sterility and high viability and recovery of hybrids.

The apparatus is readily constructed by the steps of: selecting a glass plate coated with an electrically conducting material not toxic to cells, laminating the coating with a negative photopolymer, exposing the photopolymer with ultraviolet light through a phototool defining a desired a negative of the desired electrode array, developing the photopolymer leaving the desired array covered with polymer, etching away the exposed conducting material, removing the remaining photopolymer, laminating the glass plate and electrode array with a negative photopolymer, exposing the photopolymer with a phototool masking a portion in the region of the electrode array, developing the photopolymer to define a cavity in the region of the electrode array, selecting a two surface plastic sheet, such as polycarbamate, with a protective film on each surface, removing the film from one surface and laminating it with second negative photopolymer, removing a portion of the protective films from the exposed surface of the second photopolymer in an area corresponding to the area of the cavity, developing the second photopolymer to remove material from the exposed area, removing the remainder of the protective film from the second photopolymer, forming two holes in the plastic sheet to facilitate access to the chamberthough suitable ports, laminating the plastic sheet and second photopolymer to the first photopolymer with the cavity areas in alignment.

BRIEF DESCRIPTION OF THE DRAWINGS

Further advantages and features of this invention will become apparent from the following description wherein.

DETAILED DESCRIPTION OF THE PREFERRED EMBODIMENT

This invention is directed to the design and construction of a unique apparatus in which to carry out electrofusion of cells at the optimal cell density position relative to the electric field. The apparatus also permits the use of other related techniques such as electrotransfection, selective dielectrophoresis, and electrolytic selection. This is accomplished by incorporating into the manufacturing process the ability to easily control the chamber volume, which in turn, determines the total electrode length to which the cells can be exposed. This results in a single process in which an apparatus permitting a large variety of different chamber sizes or types may be produced. The term "chamber size" is used in the context of total exposed electrode length (area). The overall design of the chambers allows usage by the standard method of electrofusion in which the cells are aligned by dielectrophoresis and fused by a direct current pulse. This design is not limited to dielectrophoresis, and may also be used by such nonstandard methods as cell alignment by magnetic fields or ultrasound waves.

Figure 1:
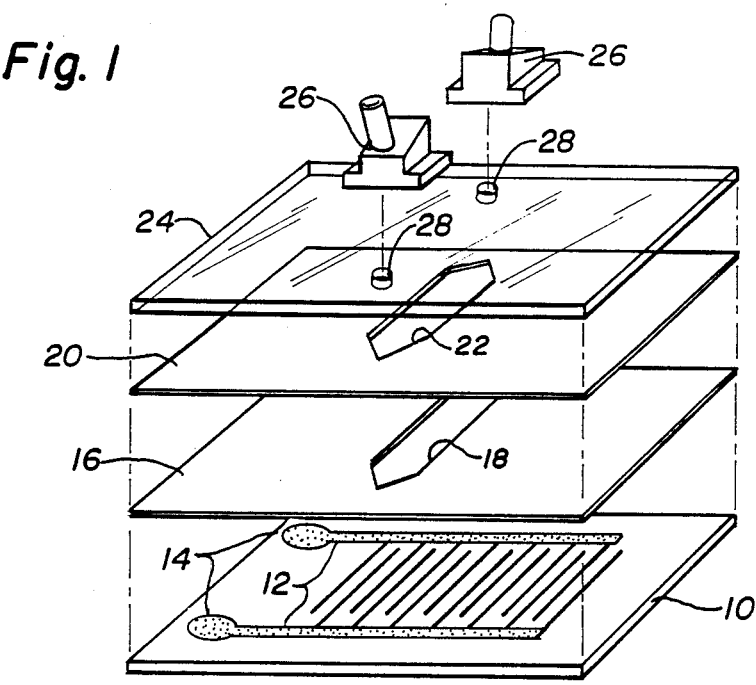
FIG. 1 is an exploded view of the apparatus of this invention.
Figure 2:
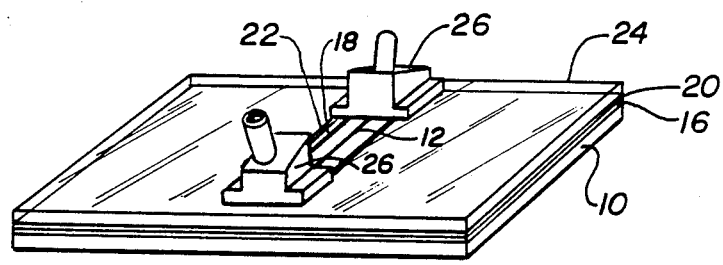
FIG. 2 is a pictorial view of the completed apparatus of this invention.
Figure 3:
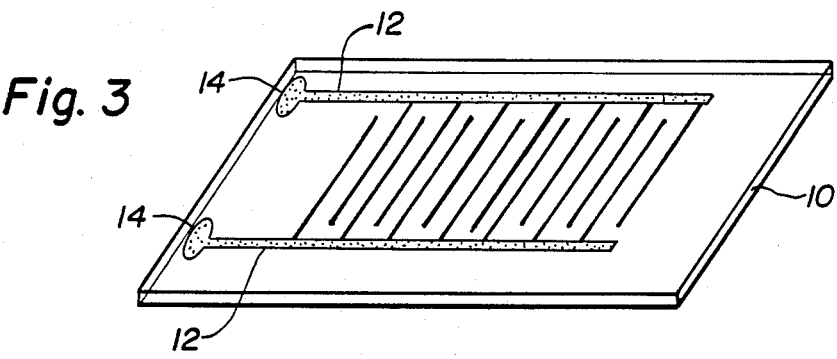
FIG. 3 shows a step of method of this invention in which a glass substrate has had the conductor material etched away to leave the opposing electrode pair.

The apparatus of fusing cells has five parts, as shown in FIGS. 1 and 2. As may be seen perhaps most clearly in FIG. 1 the apparatus is a laminate formed of a bottom planar member which is an optically clear material such as polycarbonate or glass, an array of parallel electrodes 12 which may be of a thin type, as described hereinafter, which must be nontoxic to the living cells to be fused. The electrodes 12 are connected to pads 14 for connection to external circuitry. The array is provided with alternating electrodes each alternate electrode connected to the same pad 14 so the electric fields may be created between each adjacent electrode for the purpose of electrofusion. In addition to polycarbonate, any optically clear material which is non-toxic to the cells to be fused, and preferably has some degree of flexibility may be used.

Next these electrodes may be formed of a thin, electrically conductive, film-like material that is not toxic to the cells. They must be formed by any process capable of forming them of uniform cross-section and closely spaced, i.e., down to 1-2 $\mu$m across. Conductive photopolymers may be used as well as chromium or a blend of oxides of indium and tin fused onto the glass. Gold and silver electrodes formed by suitable known processes may also be used.

The next layer of the laminate denoted by the reference numeral 16 is a photopolymer of known type such as that sold on the trademark Vacrel ™ by E. I. du Pont de Nemours and Company, Wilmington, Del. This polymer should be tough, resistant to water, not leach toxic chemicals into any water based media and finally have a high dielectric since the electric conductors are not bypassed or "shorted" by the polymer. After curing, the polymer should also maintain a constant thickness. This typically will range from 0.01 to 0.02 cm with 0.015 cm being generally preferred for many cell application. A portion 18 overlying the electrode array 12 is removed from the photopolymer 16. This removed portion will correspond to the desired flow-through chamber shape and size, the height of the photopolymer will determine the thickness of the chamber.

In a preferred embodiment the two photopolymer layers or sheets 16 and 20 are used in order to facilitate the manufacturing process and to more nearly approach the desired chamber height for most applications. Chamber height may be varied simply by selecting photopolymer sheets of different thicknesses.

The second photopolymer sheet 20 also has a cavity 22 corresponding in shape to the cavity 18 and is positioned on the sheet 20 similarly to that of the cavity 18. The apparatus is completed by a top clear plate 24. This top plate 24 has the same criteria as the lower plate 10, i.e., it should be optically transparent along with the other desired characteristics. In addition, the top plate for the purpose of facilitating manufacturing preferably should be flexible. For this reason, it is generally preferred that clear polycarbonate be used because of its flexible characteristic. Further the two polymer layers 16 and 20 should either have an existing adhesive affinity for each other and the plates 10 and 24 or be amenable to the application of a suitable adhesive.

In the preferred embodiment of this invention these polymer layers may be cured or uncured. To complete the assembly, standard Luer ports for mating the standard syringes are secured to the top surface of the upper plate 24 as by solvent welding. They are in alignment with appropriate holes 28 formed in the top plate 24 at either end of the chambers defined by voids 22 and 18. These fittings facilitate the introduction of a cell mixture into the chamber and for the elution of hybrids subsequent to fusion, under aseptic conditions. The closed design of the chamber also provides for protection from contamination during the fusion process. Although thus designed the apparatus is compact and sized to optimize the number of cells that can be subjected to the electric field even when relatively small numbers of cells are provided.

Figure 4:
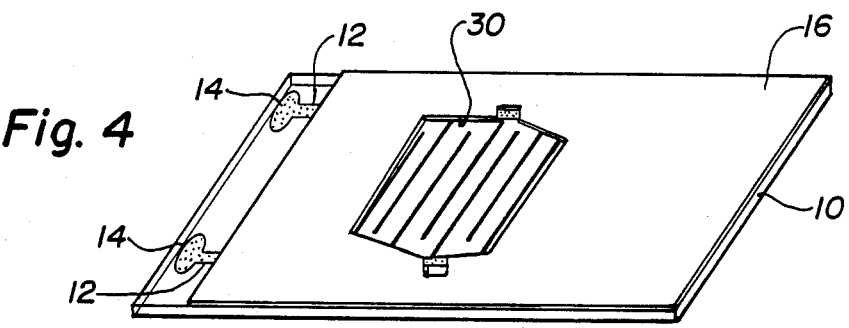
FIG. 4 schematically shows another step in the method in which a photopolymer layer laminated onto the glass substrate over the electrodes of FIG. 3.
Figure 5:
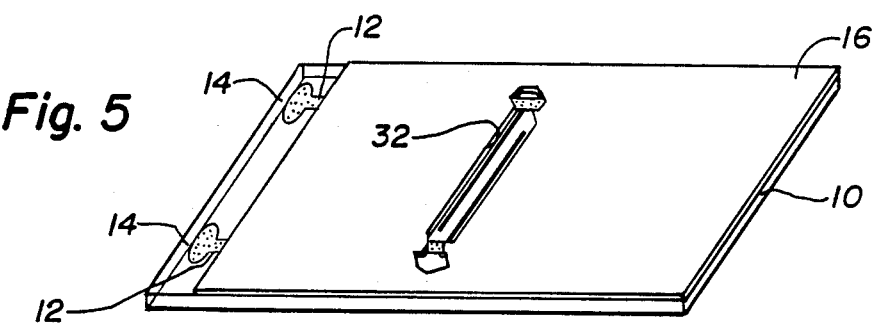
FIG. 5 is similar to FIG. 3, except that the phototool employed for the photopolymer was designed to give a flow-through chamber with a smaller effective electrode length and a smaller internal volume.

The volume of the chamber may be readily varied simply by changing the configuration of the cavities 18 and 22 formed in the polymers 16 and 20 respectively. Thus it is seen in FIG. 4 the cavity 30 may encompass a relatively large number of electrodes 12. Alternatively as is depicted in FIG. 5 the cavity 32 may be relatively small in size and only engage a pair of the electrodes 12. As will be seen most clearly in FIGS. 4 and 5 the polymer sheets 16 and 20 do not extend over the entire region of the plate 12 so as to permit the exposure of the pads 14 to facilitate electrical connection.

The use of the photopolymers allows for the production of fusion chambers that are sterile as they are assembled. This is due to the organic solvent based development steps in the processing. Organic solvents being known for the ability to lyse biological membranes, render viruses, bacteria, and fungi nonviable. Therefore, due care during this manufacturing process could obviate the need for subsequent sterilization. Additionally, the use of optically clear materials, such as the polycarbonate sheet and the glass substrate, confers upon these chambers the property of allowing for direct observation of all steps in the fusion process without compromising sterility. This is an important feature as the electronic parameters must be optimized for different cell types as well as for different cell densities.

According to the preferred method of this invention, the apparatus of FIGS. 1 and 2 is prepared by starting with a glass sheet coated with a blend of indium and tin oxides. This conductor coated glass was obtained from Donnelly Glass Co. of Holland, Mich. This sheet may be cut into pieces of appropriate size, for processing multiple electrode pairs simultaneously. These pieces were laminated with a suitable photopolymer material. Riston 218R, a product of E. I. du Pont de Nemours and Company of Wilmington, Del. is preferred.

Riston TM is a negative-working photopolymer based dry film image transfer system which photopolymer is resistant to most chemical etching processes. The availability of aqueous, semi-aqueous, and solvent processing films as well as a variety of thicknesses makes Riston TM films ideal for high resolution photomasking and etching of a wide range of substrate types.

A heated, conventional rolling lamination press may be used. The laminations should be allowed to set for 1 hour before further processing. A phototool of the desired electrode pattern 12 of FIG. 1 is drawn. A computer controlled plotter may be used for this purpose and may be drawn directly onto a translucent drafting film in opaque ink. This drawing is overlayed onto a diazo reproduction film and exposed to UV light for several seconds. The diazo film, developed using an ammonia processor provides the phototool. The photopolymer is exposed to a dose of UV light (40 millijoules in the case of the Riston 218R photopolymer). The exposed laminate is processed as recommended by the manufacturer. The developed pieces, with photopolymer remaining on the surface in a pattern corresponding to a negative of the computer drawing, are surface etched to remove the conductive coating except in the lines forming the electrode array 12. Etching of the surface may be carried out in a mixture of 50% water, 45% conc. hydrochloric acid and 5% conc. nitric acid, at 55° C. for 5 minutes. The pieces are then washed in distilled water to halt the etching and air dried. The Riston photopolymer is removed by immersion in dichloromethane for 10 min.

After drying, the pieces may be laminated with a negative photopolymer over the electrode array 12. In this case Vacrel TM made by E. I. du Pont de Nemours and Company of Wilmington, Del. is preferred.

Vacrel ® solder mask films are negative-working dry film photopolymers that are resistant to soldering processes common to the printed circuit board industry. The combination of excellent electrical properties and the high thermal resistance makes Vacrel ® films ideally suited as dielectric coatings as well as solder mask coatings. This lamination should be allowed to set for one hour before further processing. A phototool is used to define the chambers 18 and 22 dimensions, examples of which are seen in FIGS. 4 and 5. The exposure is carried out in the uv instrument described above, with the development following the manufacturers specifications. This results in a glass substrate with conductor electrodes in a defined pattern, a portion of which may be covered by the developed Vacrel layer. The layer is of a thickness designed to provide one half the desired volume to the channel. This completes the manufacture of the bottom portion of the chamber. If a single photopolymer sheet is used the top plate 24 may be secured thereto by use of a suitable adhesive and flexing the plate to eliminate any air bubbles.

Preferably the top portion of the apparatus is assembled by cutting a polycarbonate sheet 24 into pieces of the same size as the bottom plate. A sheet having protective plastic films on both surfaces is used. The plastic film is removed from one surface and laminated with a photopolymer of the type described which is nontoxic, etc., Vacrel TM being preferred. The Vacrel sheet 20 is on top of the top plate 24 and laid over the same phototool used to produce the channel on the bottom piece. The image on the phototool may be used as a guide for cutting through the mylar film on the Vacrel plate polymer thereby baring the photopolymer only in the exact shape and position of the cavity 22. With placement on the polycarbonate sheet 24 so as to leave a small margin sufficient that the contact pads 14 are uncovered when applied over the bottom plate 10. This piece is then run through the developer without any exposure to uv light. This results in the washing away of the photopolymer only in the area of the cavity 22; the rest being protected by the mylar film from the developing agent. Small holes are punched through the plastic plate 24 to correspond with the placement of the Luer fitting 26. This piece can now be taken with the remaining mylar peeled away, and carefully aligned with the cavity 18 on the bottom portion of the apparatus before being pressed firmly down. The natural adhesiveness of the undeveloped Vacrel assures a very good bond between to top and bottom portions. The protective film remaining on the top of the polycarbonate sheet 24 is removed and the Luer fitting are solvent welded over the punched holes 28 using a drop of dichloromethane. This completes the manufacture and assembly of the invention in the preferred embodiment.

By the use of thin film electrodes and photopolymer sheets, the apparatus is easily constructed with the cavity 18, 22 of a size appropriate for electrofusion, sterile, and easily adjustable in size simply by changing the phototool shape. Alternatively, the photopolymer sheet 20 may be exposed and developed, in which case a suitable adhesive is used to hold the two photopolymer sheets together.

EXAMPLE 1

Demonstration of the utility of the described chambers

A mouse was immunized in both hind footpads with 7.5 μg of the *E. coli* lipopolysacharride 0127:B8 (List Biologicals, California) emulsified in complete Freunds adjuvant (Gibco Biological Co., Michigan). Seven days later the draining popliteal lymph nodes were removed from the animal and prepared as a cell suspension. To $1.5 \times 10^8$ of these cells are added $3.03 \times 10^7$ P3 mouse myeloma cells to give a ratio of lymphocytes to myeloma cells of 5:1. The cell mixture is centrifuged to sediment the cells and the supernatant is removed by aspiration. Ten milliliters of a sterile solution of sorbitol, 0.2 M, and histidine, 0.01 M, was added to the tube which, after resuspension of the cells, was centrifuged again. This was repeated twice more until the specific conductance of the centrifuged supernatant was within 10% of the sorbitol-histidine solution. The cell mixture was resuspended at a density of $1.6 \times 10^7$ cells/ml. This suspension was taken up into a 5 ml syringe, capped and kept on ice until used.

A chamber constructed in accordance with the above method had an exposed electrode length of 311 cm total, an internal volume of 0.120 ml, and the electrodes were spaced apart 250 μm. At the cell density above, this results in a final density of $6.1 \times 10^3$ cells per cm of electrode. This density had been found to be optimal for these cell types. The conductors in this chamber were of the indium/tin oxide type. The cells were introduced into the chamber through the Luer ports, which were then capped. The chamber was then placed on the stage of an inverted tissue culture microscope and leads from a Zimmermann Electrofusion Instrument, manufactured by the GCA Corp. of Illinois were attached. Leads from a Tectronix model 2230 oscilloscope were also attached (Tecktronix Corp. of Oregon). The radio frequency supplied to the chamber was set to 1 MHz and 0 volts. While the cells were being observed through the microscope this voltage was brought up until all the cells had been observed to be aligned along the electrode edges. At this point the voltage was observed to be 4.3 volts peak to peak. Fusion of the aligned cells was induced by pressing the fusion button on the GCA instrument. This initiated a series of three direct current pulses, each of 12 us duration and of 68 volts, with a 1 second separation. The gap between the electrodes was 250 μm; this resulted in the fusion pulses being of 2.72 kv/cm. The leads were removed from the chamber which was then placed in a 37° C. incubator for 15 min.

After this period the chamber was placed in a sterile laminar air flow hood and the cells eluted into a culture tube using 13 ml of standard HAT selection medium from a 20 ml syringe. This medium consists of standard Iscove's modified Dulbecco's medium supplemented with 10% fetal calf serum (Irvine Scientific Co., Ca), hypoxanthine 0.00136 g/100 ml, thymidine 0.00076 g/100 ml, and aminopterin 0.000018 g/100 ml (all from Sigma Scientific, Mo). The cells were gently mixed by inversion of the tube, and distributed into 96 well culture plate, two drops per well. One half of the selection medium was replaced the next day. On the seventh day post fusion growing hybrid colonies were counted and found to be 143 total indicating an efficiency of $7.66 \times 10^{-5}$ or 1 hybrid per 13,426 cells. A control flask, in which unfused cells were cultured in the selective medium showed no clonal growth.

EXAMPLE 2

Fusion of cells using a flow-through chamber

A mixture of mouse splenic lymphocytes and P3 myeloma cells was prepared. The ratio of lymphocytes to P3 was 5:1, total density being $1 \times 10^7$ cells/ml. The cells were suspended in the 0.2 M sorbitol, 0.01 M histidine medium and take up into a 1 ml syringe. The syringe was mounted onto one of the Luer fittings of an electrofusion chamber consisting of a single channel 0.5 mm wide centered over the edges of two parallel electrodes spaced apart. The chamber was mounted onto the microscope stage, and electrical connection made from the GCA instrument to the contract pads. Cells were induced to flow through the chamber by pressure on the syringe plunger. Photopolymer sheets were selected during manufacture according to the preferred method of this invention so that chamber capacity was 1 μl, allowing a total of $1 \times 10^4$ cells to be in the channel at any time. The radio frequency voltage was brought up as the cells were observed to flow through the channel. Cells could be observed to align into pairs parallel to the electrical field, and normal to the direction flow through the chamber. Fusion of the flowing pairs of cells could be observed after a single D.C. pulse of 3.0 kv/cm intensity and of 15 us duration.

EXAMPLE 3

Comparison of the invention with a commercial chamber

Lymph node and P3 myeloma cells were prepared as in Example 2. The cells mixture was introduced into both a thin film chamber constructed according to the preferred method of this invention (311 cm of electrodes spaced apart 250 μm and a chamber volume of 0.12 ml) and a GCA fusion capsule (390 cm, 0.2 ml). Fusion was carried out using an alignment field of 7.5 v at 1 MHz, and a fusion pulse of 1.925 kv/cm. The fused cells were plated out as in Example 2. After 10 days of growth, the number of hybrids were counted, and found to be 28 for the thin film chamber and 3 for the GCA chamber. Calculating the efficiency of the number of hybrids obtained with respect to the total number of cells introduced into each of the chambers yields $1.5 \times 10^{-5}$ and $9.0 \times 10^{-7}$ for the chambers, respectively. This would indicate a significant increase in hybridization efficiency for the thin film chambers.

I claim:

1. An apparatus for fusing cells comprising:
   a laminate formed by a first planar member
   a grid of opposed interdigitated electrodes coated on the first member,
   a second planar member,
   a photopolymer, that is resistant to water, having a high dielectric, sandwiched between the first and second members, the photopolymer and members defining a cavity encompassing at least a portion of the opposed electrodes, means for applying electrical signals to the electrodes, and
   means in the second member defining a pair of ports for admitting liquids and cells to the chamber.

2. The apparatus of claim 1 wherein the photopolymer is sheetlike, has low leachability to chemicals toxic to living cells, and has a thickness in range of about 0.01 to about 0.02 cm.

3. The apparatus of claim 2 wherein the photopolymer has a thickness of about 0.015 cm.

4. The apparatus of claim 2 wherein the photopolymer is comprised of two sheetlike layers, each defining the cavity.

5. The apparatus of claim 4 wherein the one layer adjacent the first member is developed.

6. The apparatus of claim 5 wherein the other layer adjacent the second member is undeveloped and secures the one layer and second member together.

7. The apparatus of claim 5 where the other layer adjacent the second member is developed.

8. The apparatus of claim 1 wherein the photopolymer is comprised of two sheetlike layers, each defining the cavity.

9. The apparatus of claim 8 wherein the one layer adjacent the first member is developed.

10. The apparatus of claim 9 wherein the other layer adjacent the second member is undeveloped and secures the one layer and second member together.

11. The apparatus of claim 1 wherein the electrodes are chromium.

12. The apparatus of claim 1 wherein the electrodes are a mixture of the oxides of indium and tin.

13. The apparatus of claim 1 wherein the first member is glass.

14. The apparatus of claim 2 wherein the first member is glass.

15. The apparatus of claim 1 wherein the second member is polycarbonate.

16. The apparatus of claim 15 wherein the first member is glass.

* * * * *